(12) United States Patent
Westersten et al.

(10) Patent No.: US 7,664,545 B2
(45) Date of Patent: *Feb. 16, 2010

(54) ELECTRODE ASSEMBLY FOR CONSTANT-CURRENT ELECTROPORATION AND USE

(75) Inventors: Allan Westersten, Georgetown, CA (US); William R. Wilkinson, Scottsdale, AZ (US); Ruxandra Draghia-Akli, Houston, TX (US); Robert H. Carpenter, Bastrop, TX (US); Douglas R. Kern, The Woodlands, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 565 days.

This patent is subject to a terminal disclaimer.

(21) Appl. No.: 11/495,021

(22) Filed: Jul. 28, 2006

(65) Prior Publication Data

US 2006/0264807 A1 Nov. 23, 2006

Related U.S. Application Data

(62) Division of application No. 10/360,768, filed on Mar. 7, 2002, now Pat. No. 7,245,963.

(51) Int. Cl.
*A61N 1/30* (2006.01)

(52) U.S. Cl. .......................... 604/21; 604/20

(58) Field of Classification Search ............. 604/20, 604/21, 501; 435/173.5–173.7; 424/450, 424/455; 204/450; 607/2, 3, 72–76, 115, 607/116, 120

See application file for complete search history.

(56) References Cited

U.S. PATENT DOCUMENTS

| | | |
|---|---|---|
| 578,611 A | 3/1897 | Rively |
| 2,223,447 A | 12/1940 | Hathaway |
| 2,239,432 A | 4/1941 | Stratton |
| 2,742,041 A * | 4/1956 | Lipari ...................... 600/578 |
| 2,827,851 A | 3/1958 | Ferrara |

(Continued)

FOREIGN PATENT DOCUMENTS

| WO | WO 00/45823 | 8/2000 |
|---|---|---|
| WO | WO 01/89455 | 11/2001 |

OTHER PUBLICATIONS

Canatella, P. J. and M. R. Prausnitz. 2001. Prediction and Optimization of Gene Transfection and Drug Delivery by Electroporation. Gene Ther. 8:1464-9.

(Continued)

*Primary Examiner*—Nicholas D Lucchesi
*Assistant Examiner*—Nathan R Price
(74) *Attorney, Agent, or Firm*—Thomas S. Kim

(57) ABSTRACT

The present invention relates to a modular electrode system, and its use, for facilitating the introduction of a macromolecule into cells of a selected tissue in a body or plant. The modular electrode system comprises a non-symmetrically arranged plurality of needle electrodes; a hypodermic needle; an electrical connector that provides a conductive link from a programmable constant-current pulse controller to the plurality of needle electrodes; and a power source. In a preferred embodiment of the present invention, an operator can grasp the plurality of needle electrodes that are mounted on a support structure and firmly insert the them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses.

15 Claims, 13 Drawing Sheets

U.S. PATENT DOCUMENTS

| | | | |
|---|---|---|---|
| 2,970,545 A | | 2/1961 | Howe |
| 3,060,923 A | | 10/1962 | Reiner |
| 3,078,850 A | | 2/1963 | Schein et al. |
| 3,087,486 A | | 4/1963 | Kilpatrick |
| 3,162,592 A | | 12/1964 | Pohl |
| 3,224,436 A | | 12/1965 | Massena |
| 3,313,293 A | | 4/1967 | Chesebrough et al. |
| 3,556,099 A | * | 1/1971 | Knight et al. ............... 604/232 |
| 3,568,660 A | | 3/1971 | Crites et al. |
| 3,682,162 A | | 8/1972 | Colyer |
| 3,834,392 A | | 9/1974 | Lampman et al. |
| 3,900,020 A | | 8/1975 | Lock |
| 4,016,886 A | | 4/1977 | Doss et al. |
| 4,155,363 A | | 5/1979 | Letchworth et al. |
| 4,237,896 A | | 12/1980 | Lines |
| 4,262,672 A | | 4/1981 | Kief |
| 4,476,004 A | | 10/1984 | Pohl |
| 4,524,770 A | | 6/1985 | Orandi |
| RE32,057 E | | 12/1985 | LeVeen |
| 4,663,292 A | | 5/1987 | Wong et al. |
| 4,786,505 A | | 11/1988 | Lovgren et al. |
| 4,822,470 A | | 4/1989 | Chang |
| 4,850,956 A | | 7/1989 | Bontemps |
| 4,969,468 A | | 11/1990 | Byers et al. |
| 4,970,154 A | | 11/1990 | Chang |
| 5,019,034 A | | 5/1991 | Weaver et al. |
| 5,137,817 A | | 8/1992 | Busta et al. |
| 5,273,525 A | * | 12/1993 | Hofmann ..................... 604/21 |
| 5,389,069 A | | 2/1995 | Weaver |
| 5,439,440 A | | 8/1995 | Hofmann |
| 5,462,520 A | | 10/1995 | Hofmann |
| 5,464,386 A | | 11/1995 | Hofmann |
| 5,468,223 A | | 11/1995 | Mir |
| 5,501,662 A | | 3/1996 | Hofmann |
| 5,507,724 A | | 4/1996 | Hofmann et al. |
| 5,545,130 A | | 8/1996 | Hofmann et al. |
| 5,580,859 A | | 12/1996 | Felgner et al. |
| 5,628,728 A | | 5/1997 | Tachibana et al. |
| 5,676,646 A | | 10/1997 | Hofmann et al. |
| 5,688,233 A | | 11/1997 | Hofmann et al. |
| 5,702,359 A | | 12/1997 | Hofmann et al. |
| 5,704,908 A | | 1/1998 | Hofmann et al. |
| 5,727,808 A | | 3/1998 | Broughton |
| 5,810,762 A | | 9/1998 | Hofmann |
| 5,859,327 A | | 1/1999 | Dev et al. |
| 5,869,326 A | | 2/1999 | Hofmann |
| 5,873,849 A | | 2/1999 | Bernard |
| 5,944,710 A | | 8/1999 | Dev et al. |
| 5,968,006 A | | 10/1999 | Hofmann |
| 5,968,895 A | * | 10/1999 | Gefter et al. .................. 514/2 |
| 6,006,130 A | | 12/1999 | Higo et al. |
| 6,068,650 A | | 5/2000 | Hofmann et al. |
| 6,096,020 A | | 8/2000 | Hofmann et al. |
| 6,110,161 A | * | 8/2000 | Mathiesen et al. .......... 604/500 |
| 6,120,493 A | | 9/2000 | Hofmann et al. |
| 6,150,148 A | | 11/2000 | Nanda et al. |
| 6,181,964 B1 | | 1/2001 | Hofmann et al. |
| 6,192,270 B1 | | 2/2001 | Hofmann et al. |
| 6,208,893 B1 | | 3/2001 | Hofmann et al. |
| 6,216,034 B1 | | 4/2001 | Hofmann et al. |
| 6,233,482 B1 | | 5/2001 | Hofmann et al. |
| 6,241,701 B1 | | 6/2001 | Hofmann et al. |
| 6,259,946 B1 | | 7/2001 | Higo et al. |
| 6,278,895 B1 | | 8/2001 | Bernard |
| 6,300,108 B1 | | 10/2001 | Rubinsky et al. |
| 6,302,874 B1 | | 10/2001 | Zhang et al. |
| 6,314,316 B1 | | 11/2001 | Gilbert et al. |
| 6,928,318 B2 | * | 8/2005 | Simon ......................... 604/20 |
| 2002/0025578 A1 | | 2/2002 | MacLaughlin et al. |
| 2002/0038112 A1 | | 3/2002 | Mathiesen et al. |
| 2002/0198485 A1 | | 12/2002 | Dev et al. |

OTHER PUBLICATIONS

Dean, D.A., D. Machado-Aranda, K. Blair-Parks, A.V. Yeldandi, and J.L. Young. 2003. Electroporation as a method for high-level nonviral gene transfer to the lung. Gene Ther. 10:1608-1615.

Draghia-Akli, R., K. K. Cummings, A. S. Khan, P. A. Brown, and R. H. Carpenter. 2003a. Effects of plasmid-mediated growth hormone releasing hormone supplementation in young healthy Beagle dogs. Journal of Animal Science 81:2301-2310.

Draghia-Akli, R., K. M. Ellis, L. A. Hill, P. B. Malone, and M. L. Fiorotto. 2003b. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., A. S. Khan, K. K. Cummings, D. Parghi, R. H. Carpenter, and P. A. Brown. 2002. Electrical Enhancement of Formulated Plasmid Delivery in Animals. Technology in Cancer Research & Treatment 1:365-371.

Fattori, E., N. La Monica, G. Ciliberto, and C. Toniatti. 2002. Electrogene-transfer: a new approach for muscle gene delivery. Somat. Cell Mol. Genet. 27:75-83.

Lee, R. C., D. Zhang, and J. Hannig. 2000. Biophysical injury mechanisms in electrical shock trauma. Annu. Rev. Biomed. Eng 2:477-509.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Martin, G. T., U. F. Pliquett, and J. C. Weaver. 2002. Theoretical analysis of localized heating in human skin subjected to high voltage pulses. Bioelectrochemistry. 57:55-64.

McMahon, J.M., E. Signori, K.E. Wells, V.M. Fazio, and D.J. Wells. 2001. Optimization of Electrotransfer of Plasmid into Skeletal Muscle by Pretreatment with Hyaluronidase—Increased Expression with Reduced Muscle Damage. Gene Ther. 8:1264-70.

Mir, L. M., M. F. Bureau, J. Gehl, R. Rangara, D. Rouy, J. M. Caillaud, P. Delaere, D. Branellec, B. Schwartz, and D. Scherman. 1999. High-efficiency gene transfer into skeletal muscle mediated by electric pulses. Proc. Natl. Acad. Sci. U. S. A 96:4262-4267.

Mir, L. M., M. F. Bureau, R. Rangara, B. Schwartz, and D. Scherman. 1998. Long-term, high level in vivo gene expression after electric pulse-mediated gene transfer into skeletal muscle. C. R. Acad. Sci. III 321:893-899.

Mor, G. and M. Eliza. 2001. Plasmid DNA vaccines. Immunology, tolerance, and autoimmunity. Mol. Biotechnol. 19:245-250.

Pilaro, A. M. and M. A. Serabian. 1999. Preclinical development strategies for novel gene therapeutic products. Toxicol. Pathol. 27:4-7.

Pliquett, U. F., G. T. Martin, and J. C. Weaver. 2002. Kinetics of the temperature rise within human stratum corneum during electroporation and pulsed high-voltage iontophoresis. Bioelectrochemistry. 57:65-72.

Stoll, S. M. and M. P. Calos. 2002. Extrachromosomal plasmid vectors for gene therapy. Curr. Opin. Mol. Ther. 4:299-305.

International Search Report, International Application No. PCT/US 03/06833, Jul. 28, 2004.

* cited by examiner

1 – needle mounting bracket
2 – cannula for delivering macromolecules
3 – needle electrode
4 – electrical connection to circuit
5 – Programmable current pulse controller
6 – Siding needle guide 1 – Handle
2 – Syringe
3 – Needle electrode assembly
4 – electrical connection to circuit

ELECTRODE ASSEMBLY FOR CONSTANT-CURRENT ELECTROPORATION AND USE

RELATED APPLICATIONS

This application is a divisional application of U.S. application Ser. No. 10/360,768, filed Mar. 7, 2002, now U.S. Pat. No. 7,245,963, entitled "Electrode Assembly for Constant Current Electroporation and Use," the entire content of which is hereby incorporated by reference.

BACKGROUND

The present invention relates to a modular electrode system, and its use, for facilitating the introduction of a macromolecule into cells of a selected tissue in a body or plant. The modular electrode system comprises a plurality of non-symmetrically arranged needle electrodes; a hypodermic needle; an electrical connector that provides a conductive link from a programmable constant-current pulse controller to the plurality of needle electrodes; an impedance meter; and a power source. In a preferred embodiment of the present invention, an operator can grasp the plurality of needle electrodes that are mounted on a support structure and firmly insert the them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is prevented by limiting the current to levels that do not cause excessive heating.

Broadly, electroporation is the use of a transmembrane electric field pulse to induce microscopic pathways (pores) in a bio-membrane. These pores are commonly called "electropores." Their presence allows macromolecules, ions, and water to pass from one side of the membrane to the other. Thus, electroporation has been used to introduce drugs, DNA or other molecules into multi-cellular tissues, and may prove to be an effective for the treatment of certain diseases. However, the use of electroporation in living organisms has several problems, including cell death that results from generated heat and the inability of electropores to reseal. The beneficial effects of the drug or macromolecule are extremely limited with prior art electroporation methods where excessive cell heating and cell death occurs.

To better understand the process of electroporation, it is important to look at some simple equations. When a potential difference (voltage) is applied across the electrodes implanted in a tissue, it generates an electric field ("E"), which is the applied voltage ("V") divided by the distance ("d") between the electrodes.

$$E = V/d$$

The electric field intensity E has been a very important value in prior art when formulating electroporation protocols for the delivery of a drug or macromolecule into the cell of the subject. The field intensity is inversely proportional to the distance between the electrode in that given a voltage, the field strength increases as the distance between the electrodes is decreased. However, a caveat is that an electric field can be generated in a tissue with insulated electrodes (i.e. flow of ions is not necessary to create an electric field). Although not wanting to be bound by theory, it is the flow of ions that opens the electropores and allows movement of molecules into the cells of a subject during electroporation. The flow of electric charge in a conductor or medium between two points having a difference in potential is called the current. The current between electrodes is achieved by the ions or charged particles in the tissues, which can vary among tissues and patients. Furthermore, the flow of conducting ions in the tissue can change between electrodes from the beginning of the electric pulse to the end of the electric pulse.

When tissues have a small proportion conducting ions, resistance is increased, heat is generated and cells are killed. Ohm's law expresses the relationship between current ("I"), voltage ("V"), and resistance ("R"):

$$R = V/I$$

The resistance in the tissue between two electrodes varies depending on the charged particles present therein, thus, the resistance in the tissue changes from the beginning of the electric pulse to the end of the electric pulse.

Heating is the product of the inter-electrode impedance (i.e. combination of resistance and reactance and is measured in ohms), and is proportional to the product of the current, voltage and pulse duration. Heating can also be expressed as the square of the current, and pulse duration ("t", time). For example, during electroporation the heating or power ("W", watts) generated in the supporting tissue can be represented by the following equation:

$$W = I^2 R t$$

Broadly, prior art teaches that metallic electrodes are placed in contact with tissues and short pulses of predetermined voltages are imposed on the electrodes initiating the cells to transiently open membrane pores. The protocols currently described for electroporation are defined in terms of the resulting field intensities E, which are dependent on short pulses of voltage proportional to the distance between the electrodes, and regardless of current. Accordingly, the resistance or heating cannot be determined for the electroporated tissue, which leads to varied success with different pulsed voltage electroporation protocols. Certainly, the difference in upper limit amplitudes of a voltage pulse between electroporation protocols that facilitate effective electroporation and electroporation protocols that cause the cells to die are very small. Additionally, a definite correlation has been observed between death of cells and the heating of cells caused by the upper limit amplitudes of the short voltage pulses. Thus, the over heating of cells between across electrodes serves as a principal cause for the ineffectiveness of any given electroporation voltage pulsing protocol. Furthermore, the current between electrodes serves as a primary determinant of the effectiveness of any given pulsing protocol, not the voltage across the electrodes.

When electricity is delivered to the cells of a subject, the dose of electricity can be accurately described in terms of charge ("Q"), which is the current ("I") and the time ("t"), according to the formula:

$$Q = It$$

If the current is not constant, as is the case in prior art electroporators, Q represents the time integral of I. In this respect, charged particles, be they ions or molecules, behave in a similar fashion. For example, when silver ions are deposited on an electrode to define the standard unit of electrical charge (the coulomb), only the charge, as defined above, is of importance. A certain minimum voltage must be present to generate a current, but the quantity of ions deposited can not be determined from a pre-determined voltage. Correspondingly, the quantity of charged particles delivered to cells in an electroporator can not be derived from the voltage imposed on the electrodes.

Although electroporation is widely used for laboratory gene transfection and gaining increased importance for non-viral gene therapy, it is generally employed using trial-and-error optimization schemes for lack of methods to predict electroporation's effects on cells (Canatella P J, *Gene Ther* October 2001; 8(19):1464-9). For example, it has been shown that the efficiency of plasmid gene transfer to skeletal muscle can be significantly improved by the application of an electrical field to the muscle following injection of plasmid DNA. However, this electrotransfer is associated with significant muscle damage that may result in substantial loss of transfected muscle fibers (McMahon J M, Signori E, Wells K E, Fazio V M, Wells D J. *Gene Ther* August 2001; 8(16):1264-70). The reduction of the voltage used in the technique can result in a decrease in muscle damage, with a concomitant reduction in expression, but without a significant decrease in the number of transfected fibers.

The effectiveness of electroporation is limited by the fact that there is a threshold value for the pulse intensity below which electroporation does not occur, and an upper limit above which the cells are destroyed.

Experimental evidence shows that the difference between the upper and lower limits is so small that it is very difficult to design effective pulsing protocols without undue experimentation. This makes use of the technique difficult.

References in the art directed toward an electroporation apparatus illustrate the usefulness of both an electrode apparatus and an in vivo method of electroporation. Correspondingly there are many U.S. Patents that claim either specific electrodes, or methods for electroporation. For example, U.S. Pat. No. 6,302,874 is a method and apparatus for electrically assisted topical delivery of agents for cosmetic applications; U.S. Pat. No. 5,676,646; is a flow through electroporation apparatus for implanting molecules into living blood cells of a patient; U.S. Pat. Nos. 6,241,701 & 6,233,482 describes a method and apparatus for electroporation mediated delivery of drugs and genes. More specifically they describe a method and apparatus for electroporation therapy ("EPT") for treating tumors treated by a combination of electroporation using the apparatus of the invention and a chemotherapeutic agent caused regression of tumors in vivo; U.S. Pat. No. 6,216,034; describes a method of programming an array of needle electrodes for electroporation therapy of tissue; U.S. Pat. No. 6,208,893; describes an electroporation apparatus with a connective electrode template; U.S. Pat. No. 6,192,270; Describes an electrode assembly for an apparatus and a method of trans-surface molecular delivery; U.S. Pat. No. 6,181,964, describes a minimally invasive apparatus and method to electroporate drugs and genes into tissue. Using electroporation therapy ("EPT") as described in the invention, tumors treated by a combination of electroporation using the apparatus of the invention and a chemotherapeutic agent caused regression of tumors in vivo; U.S. Pat. No. 6,150,148, describes an electroporation apparatus for control of temperature during the process, by generating and applying an electric field according to a user-specified pulsing and temperature profile scheme; U.S. Pat. No. 6,120,493, describes a method for the introduction of therapeutic agents utilizing an electric field electroporation apparatus; U.S. Pat. No. 6,096,020, describes an electroporation method and apparatus generating and applying an electric field according to a user-specified pulsing scheme; U.S. Pat. No. 6,068,650, describes a method of selectively applying needle array configurations for in vivo electroporation therapy; and U.S. Pat. No. 5,702,359, describes an electrode apparatus for the application of electroporation to a portion of the body of a patient with a sensing element for sensing a distance between the electrodes and generating a distance signal proportionate to the distance between said electrodes, and means responsive to said distance signal for applying pulses of high amplitude electric signal to the electrodes proportionate to the distance between said electrodes. All of these cited patents are hereby incorporated by reference The aforementioned patent disclosures along with many others describe electroporators and methods for use by utilizing a predetermined voltage between the electrodes. Because the impedance between electrodes that are embedded in a tissue can vary from case-to-case, or tissue-to-tissue, a predetermined voltage does not produce a predetermined current. Thus, prior art does not provide a means to delineate the exact dosage of current to which the cells are exposed and limits the usefulness of the electroporation technique. For this very reason, conventional electroporators generate tremendous amounts of heat is tissues that can easily kill cells. For example, a typical electronic 50 ms pulse with an average current of 5 Amperes across a typical load impedance of 25 ohms can theoretically raise the temperature in tissue 7.5° C., which enough to kill cells. In contrast, the power dissipation decreases in a constant-current system and prevents heating of a tissue, which reduces tissue damage and contributes to the overall success of the procedure.

The difficulties present in prior-art electrodes stem from the fact that the pulse energy is concentrated in the center of the array, the point where the material to be transfected is deposited.

As a result, the spatial distribution of energy delivery assumes a very non-uniform character. Therefore, only a fraction of the cells in the volume encompassed by the electrode assembly is electroporated.

Thus, there is a need to overcome the problems of prior art by providing a means to effectively control the dosage of electricity delivered to the cells in the inter-electrode space by precisely controlling the ionic flux that impinges on the conduits in the cell membranes.

SUMMARY

One object of this invention is to provide an electrode system for electroporation that facilitates the delivery of electrical energy to tissues in a manner that assures that the energy dose delivered lies consistently between the upper and lower limits, thereby providing increased electroporation efficiencies.

Yet another object of the present invention is to provide an electrode system for electroporation having a configuration of pin electrodes whereby the electroporation pulse is directed between two or more electrodes such that the direct line between any two electrodes does not pass through the center of the injected macromolecule. This is to minimize the number of cells that are under energized and thus not electroporated and the number of cells which are over energized and thus destroyed while at the same time maximizing the number of cells that lie between these extremes which are adequately energized and thus electroporated.

Still another object of the present invention is to provide a small sealed unit dose carrier, which accepts a standard luer or other geometric configuration from a syringe or other suitable injection devise on the inlet end of the carrier. The carrier further accepts a standard luer or other geometric configuration of a hypodermic needle or other suitable introducer on the outlet end of the carrier. The carrier can then be attached to a syringe containing saline or other suitable perfusate and to a needle at its other end and the saline can be used to flush all of the expensive macromolecule in the container into the living tissue.

Another object of the present invention is to provide an electrode system for electroporation having uniform pulse energy distribution.

One embodiment of the present invention pertains to a modular electrode system for facilitating the introduction of a macromolecule into cells of a selected tissue in a body or plant. The modular electrode system comprises a plurality of needle electrodes; a hypodermic needle; an electrical connector that provides a conductive link from a programmable constant-current pulse controller to the plurality of needle electrodes; and a power source of alternating current or direct current. The plurality of needle electrodes are mounted on a support structure with a configuration for penetrating the selected tissue. In a preferred embodiment, the macromolecule are injected into the selected tissue with a syringe. Together the plurality of needle electrodes and support structure form a needle electrode assembly that can be mounted on a non-conductive handle. The handle houses an electrical connector from the needle electrode assembly to a constant-current pulse generator subsystem. The handle is designed to provide a user an easy means for implanting the needle electrode assembly into a selected tissue. The utilization of disposable needle electrode assembly, a single dose macromolecule injection cartridge with needle, and quick-release mounts on the handle allows the user to quickly attach and detach the needle electrode assembly.

The constant-current pulse generator subsystem provides constant-current pulses between at least any two electrodes of the needle electrode assembly. The constant-current pulse generator subsystem can deliver a decentralized constant-current pulse to an area of a tissue such that electroporation overlap points to not develop. Furthermore, the utilization of a constant-current pulse has several advantages over prior art, one advantage being reduced heating and subsequent death of the electroporated tissue. A further embodiment of the present invention allows the entire modular electrode system to be portable and operated via a battery pack.

Another embodiment of the present invention is a method for facilitating the transport of a macromolecule into cells of a selected tissue in the body or plant. Briefly, an operator can grasp the plurality of needle electrodes that are mounted on a support structure and firmly insert the them into the selected tissue in a body or plant. The macromolecules are then delivered via the injection needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is prevented by keeping the constant-current below a certain critical value.

DETAILED DESCRIPTION OF PREFERRED EMBODIMENTS

Figure 1:
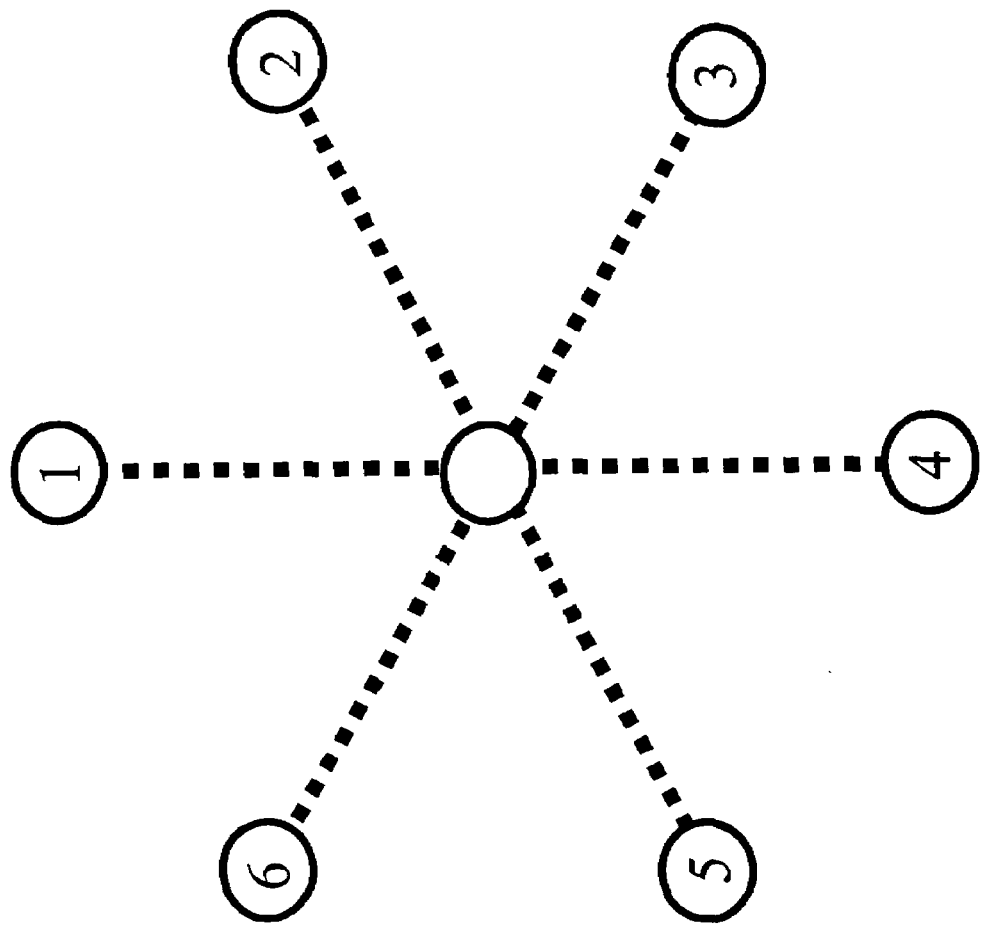
FIG. 1 shows an electrode array of the prior art using six electrodes in three opposed pairs. It further depicts a single centralized electroporation overlap point, which is the center point of the asterisk pattern illustrated.

The term "current" as used herein refers to the flow or rate of flow of electric charge in a conductor or medium between two points having a difference in potential, generally expressed in amperes The term "ampere" as used herein refers to the standard unit for measuring the strength of an electric current; rate of flow of charge in a conductor or conducting medium of one coulomb per second The term "coulomb" as used herein refers to the meter-kilogram-second unit of electric charge equal in magnitude to the charge of $6.28 \times 10^{18}$ electrons; charge transported through a conductor by a current of one ampere flowing for one second The term "voltage" as used herein refers to the electromotive force, or difference in electrical potential, expressed in volts, which are the practical units of electromotive force or difference in potential between two points in an electric field that requires one joule of work to move a positive charge of one coulomb from the point of lower potential to the point of higher potential.

The term "power" as used herein refers to a source of physical or mechanical force or energy; force or energy that is at, or can be put to, work, "electric power, waterpower"

The term "impedance" as used herein refers to the total opposition offered by an electric circuit to the flow of an alternating current of a single frequency: it is a combination of resistance and reactance and is measured in ohms.

The term "field" as used herein refers to physical quantity specified at points throughout a region of space.

The term "quick-release mechanism" as used herein refers to any connector mechanism that allows the plurality of needle electrodes to be fastened securely and released quickly from the constant-current pulse generator subsystem. When the needle electrodes are fastened securely, the quick release mechanism also maintains electrical communication with the constant-current pulse generator subsystem. Many different types of quick-release mechanisms are well known in the art of engineering.

The term "amplitude" as used herein refers to the extreme range of a fluctuating quantity, as an alternating current or the swing of a pendulum, generally measured from the average or mean to the extreme. It is the quality of being ample or the amount or degree to which a thing extends.

The term "frequency" as used herein refers to the number of periodic oscillations, vibrations, or waves per unit of time: usually expressed in hertz.

The term "macromolecule" as used herein refers to nucleic acid sequences, proteins, lipids, microbubbles (e.g. drug-loaded vesicles), and pharmaceuticals The present invention relates to a modular electrode system for facilitating the introduction of a macromolecule into cells of a selected tissue in a body or plant. The modular electrode system comprises a plurality of needle electrodes; a needle; an electrical connector that provides a conductive link from a programmable constant-current pulse controller to the plurality of needle electrodes; and a power source, either alternating current ("AC") or direct current ("DC"). In a preferred embodiment of the present invention, an operator can grasp the plurality of needle electrodes that are mounted on a support structure and firmly insert the them into the selected tissue in a body or plant. The macromolecules are then delivered via the needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is prevented by utilizing an impedance meter built into the programmable constant-current pulse controller. As the impedance rises in the selected tissue during a constant-current pulse, the power is reduced accordingly to maintain a constant-current, and to prevent cell death due to overheating. Thus, the utilization of a constant-current pulse has several advantages over prior art.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances, maintain a resting transmembrane potential of ca. 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula $E=V/d$, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

Figure 2:
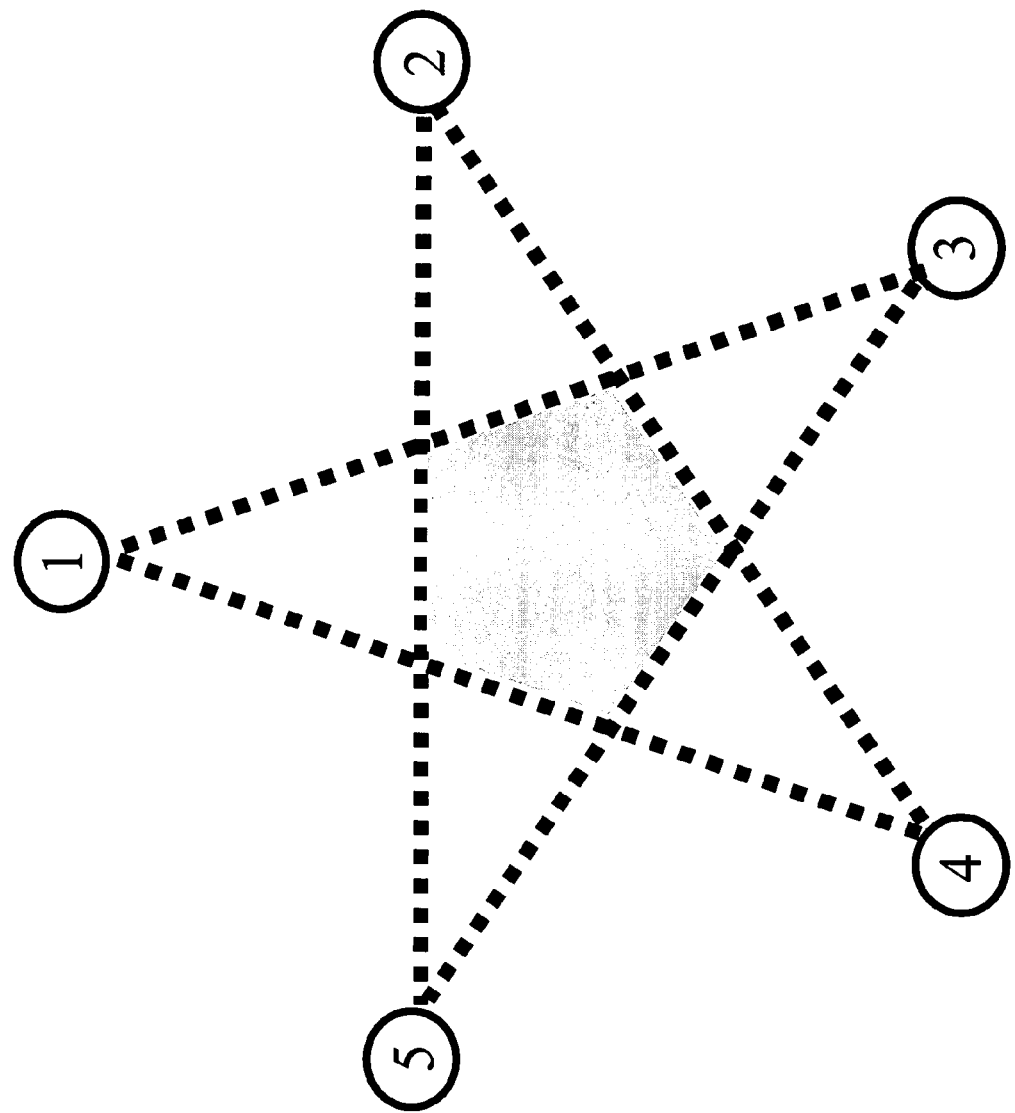
FIG. 2 shows one electrode array of the present invention using five electrodes. It further depicts how a symmetrically arranged needle electrode array without opposing pairs can produce a decentralized pattern during an electroporation event in an area where no congruent electroporation overlap points develop and how an area of the decentralized pattern resembles a pentagon.

During electroporation, the heat produced is the product of the interelectrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop, and can be visualized as an asterisk pattern as shown in FIG. 1. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop. One example of such symmetry is shown in FIG. 2, which shows the decentralized pattern area of electroporation that resembles a pentagon.

Controlling the current flow between electrodes allows one to determine the relative heating of cells. Thus, it is the current that determines the subsequent effectiveness of any given pulsing protocol, and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

Figure 3:
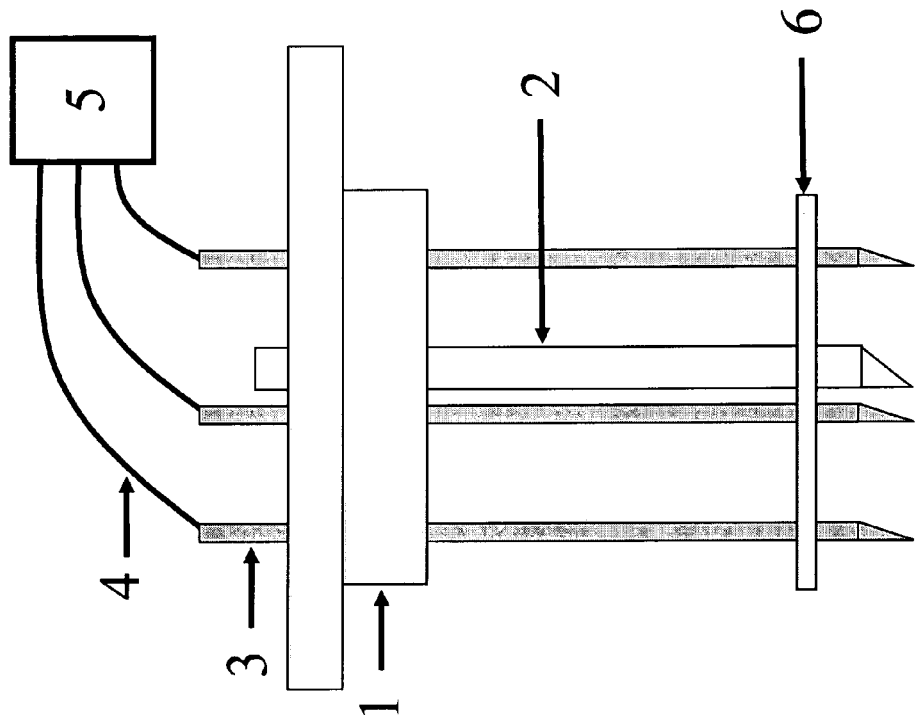
FIG. 3 shows one electrode assembly array with needle mounting bracket, and sliding needle guide.
Figure 3:
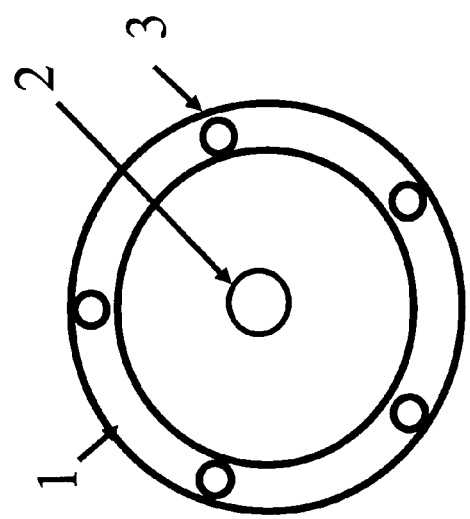
Figure 4:
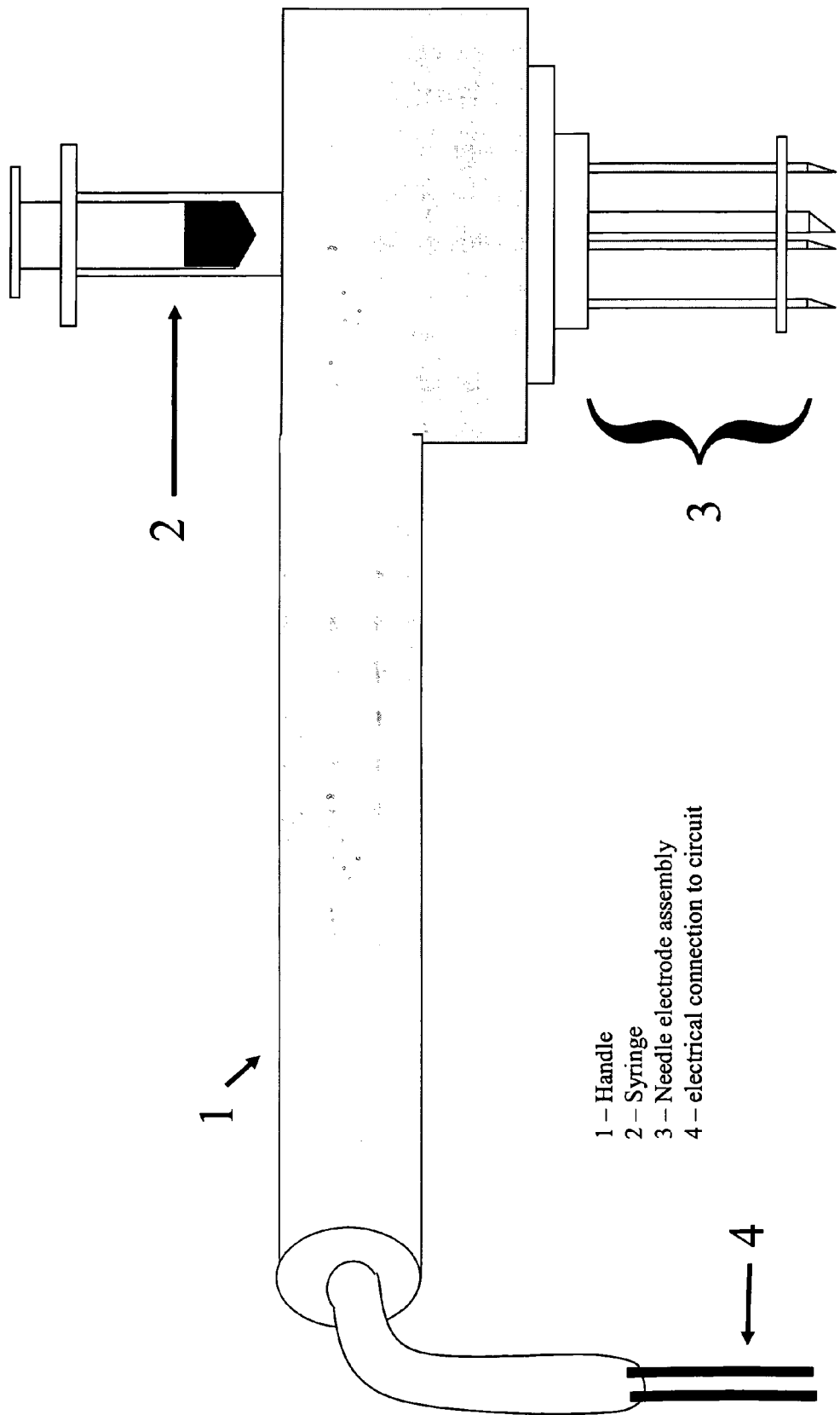
FIG. 4 shows a representation of an electrical connector handle assembly with a mount structure for needle electrode assembly, and a syringe. This figure also indicates the electrical connections from the programmable circuit to the needle electrode assembly.
Figure 5:
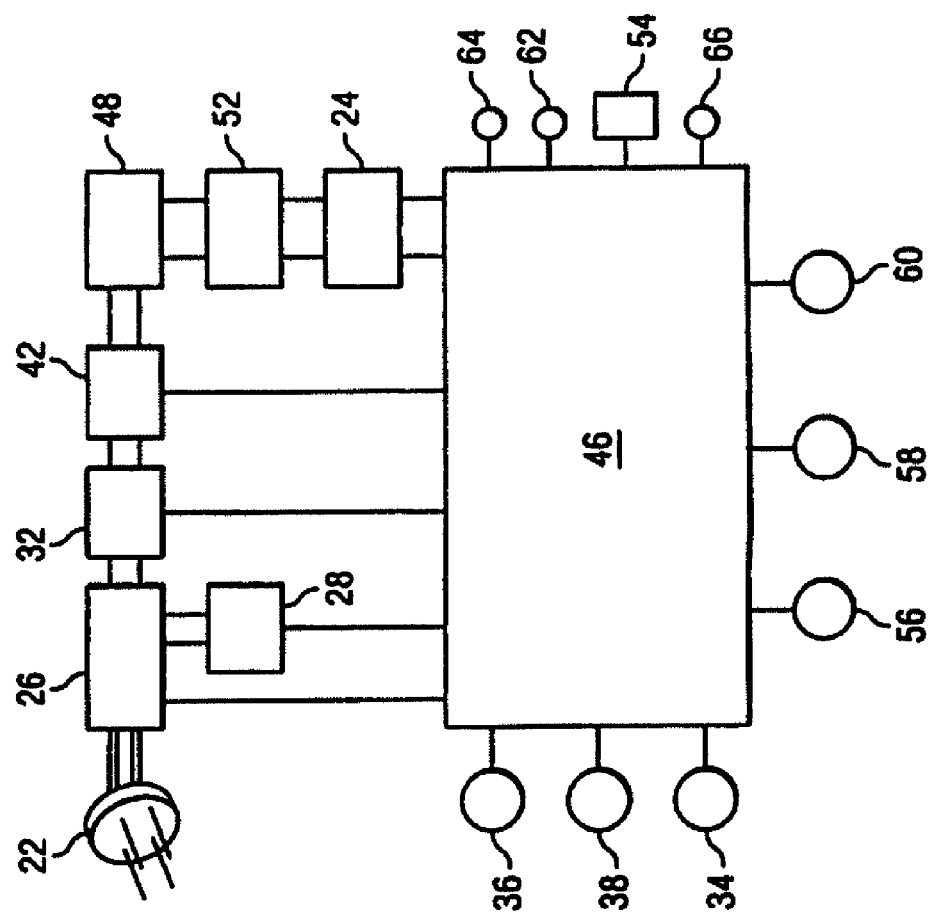
FIG. 5 shows a block diagram of a programmable constant-current pulse circuit in electrical communication with the needle electrode assembly and a power source.

One embodiment of the present invention to overcome the above problem by providing a means to effectively control the dosage of electricity delivered to the cells in the inter-electrode space by precisely controlling the ionic flux that impinges on the conduits in the cell membranes. Thus, the precise dosage of electricity to tissues can be calculated as the product of the current level, the pulse length and the number of pulses delivered. In order to implement such a constant-current system, an electrode apparatus (as shown in FIGS. 3 and 4) connected to a specially designed circuit. (as shown in FIG. 5) must be considered.

One goal of the present invention to provide a means to deliver the electroporative current to a volume of tissue along a plurality of paths without, causing excessive concentration of cumulative current in any one location, thereby avoiding cell death owing to overheating of the tissue. For example, the maximal energy delivery from a particular pulse would occur along a line that connects two electrodes. Prior art teaches that the electrodes are present in pairs and that the voltage pulses are delivered to the paired electrodes of opposed polarity. Accordingly, the maximal energy delivery from a particular pulse would occur along a line that connects two electrodes. An example of the energy delivery pathway in a prior art electrode, which utilizes three pairs of radial electrodes with a center electrode, is described above and as in FIG. 1. A distribution of the energy crosses at the center point of the electrodes, which may lead to unnecessary heating and decreased survival of cells.

The electrodes of one embodiment of the present invention are arranged in a radial and symmetrical array, but unlike prior art, the electrodes are odd numbered, and not in opposing pairs (FIG. 2). Delivering an electric pulse to any two of the electrodes from an electric pulse generator results in a pattern that is best described as a polygon. Tracing this pattern would result in a five-point star with a pentagon of electrical pulses surrounding the center of the array in tissue where the concentration of molecules to be transfected is greatest. Although not wanting to be bound by theory, it is not the odd number of electrodes, per se, that makes a difference, but in the direction of the current paths. With the configuration of prior art, all the pulses generate a current that passes through the center of the assembly. The cumulated dose, i.e. the heating effect is therefore concentrated in the center, with the peripheral dose falling off rapidly. With the "five-pointed star" arrangement, the dose is spread more evenly, over a larger volume. For example, if the electrodes are arranged in an array of five electrodes, the pulses might be sequentially applied to electrodes 1 and 3, then 3 and 5, then 5 and 2, then 2 and 4, then 4 and 1. However, because the tissue between the electrodes is a volume conductor, a certain current intensity exists along parallel lines, weakening as the distance from the center line increases. The cumulative effect of a sequence of pulses results in a more uniform distribution of the energy delivered to the tissues, increasing the probability that the cells that have been electroporated actually survive the procedure.

Referring to FIG. 3, a needle electrode assembly in accordance with one embodiment of the invention is illustrated. The electrode assembly comprises a plurality needle electrodes 3 that are supported by a mounting bracket for the needle electrodes 1, and a sliding needle guide 6. In the center of the circular array of needle electrodes is a syringe 2 for injecting macromolecules into the tissue and is not electrically connected to the programmable current pulse controller 5. Each needle electrode is electrically connected to 4 to the programmable current pulse controller 5. Once all needle electrodes are adjusted to an appropriate penetration depth for a particular tissue, the mounting bracket is grasped and needle electrodes are inserted into the proper tissue. To prevent the needle electrodes from bending as the assembly is pressed into the tissue a sliding needle guide is used. The needle electrodes 1 are in electrical communication with the programmable current pulse controller 5. A suitable quantity of macromolecules are then delivered to the tissue in the center of the needle electrode array through the cannula 2.

It is know in prior art that the nature of the voltage pulse to be generated is determine by the nature of tissue, the size of the selected tissue and distance between electrodes. It is desirable that the voltage pulse be as homogenous as possible and of the correct amplitude. Excessive field strength results in the lysing of cells, whereas a low field strength results in reduced efficacy of electroporation. Prior art inventions utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternative embodiment of the needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

The needle electrode assemblies, as described above, enable the in vivo positioning of electrodes in or adjacent to tumors without the need to determine the distance between electrodes for the purpose of calculating electric field or voltage pulses. Thus, another embodiment of the present invention is simplified electrochemotherapy.

The current strength, the pulse length and the number of pulses delivered can be determined by the operator and do not vary with the characteristics of different tissues or variations of the electrode impedance from case to case. Thus, owing to the inherent repeatability of the constant-current system, effective protocols for electroporation can be developed.

The method also provides a simple means for determining the temperature elevation of the tissues exposed to the pulses. The product of the measured inter-electrode impedance, the square of the current and the cumulated pulse duration is a measure of the total energy delivered. This quantity can be converted to degrees Celsius, when the volume of the tissues encompassed by the electrodes and the specific heat of the tissues are known. For example the rise in tissue temperature ("T", Celsius) is the resistance ("R", ohms), current ("I", Amperes), length of pulse ("t", seconds), and the conversion factor between joules and calories ("K"). $T=RI^2tK$.

At the moment of electroporation, the current increases in a prior art system where a predetermined voltage has been imposed on the electrodes, owing to the fact that increased cell permeability lowers the interelectrode impedance. This may lead to an excessive temperature rise, resulting in cell death. For example, utilizing values common for conventional electroporators, and assuming that the volume enclosed by the electrodes is one cubic centimeter and the specific heat of the tissues is close to unity, the temperature rise owing to one 50 mS pulse with an average current of 5 Amperes across a typical load impedance of 25 ohms is ca 7.5° C. This points out the necessity of inserting an adequate delay between successive pulses, to allow the subjects circulatory system to remove enough heat so that the cumulative temperature rise will not result in destruction of the tissues being electroporated.

The advantage of a constant-current is that it can be prevented from attaining an amplitude at which the cells are destroyed. In a predetermined voltage system, the current can attain a destructive intensity, and the operator can not prevent that from happening. In a constant-current system, the current is preset under a threshold level where cell death does not occur. The exact setting of the current is dependent of the electrode configuration, and it must be determined experimentally. However, once the proper level has been determined, cell survival is assured, from case to case.

A specially designed circuit was considered, and is outlined in FIG. 5, and described below. Although the building blocks of such a circuit can be implemented by technology known to any person skilled in the art of electronics, the block design FIG. 5 required to deliver a constant-current to an electroporation apparatus requires insight to how electric currents effect living cells.

In FIG. 5, the electrode assembly 22 is connected to selector switch 26, which is connects the electrodes to ohm meter 28 in any sequence, as directed by controller 46. Switch 26 can also connect the electrodes to current switch 32, which delivers current pulses to the electrodes from constant-current source 42. The voltage required to operate constant-current source 42 is generated by high-voltage supply 48, and the voltage required to operate the controller is generated by low-voltage supply 24. The energy is being delivered to both supplies by battery 52.

User-settable input devices 34, 36 and 38 provide means for the user to specify the current level, the pulse length and the pulse count, respectively. The ENABLE button 56 initiates the operation of the device by directing the controller to measure the inter-electrode impedance when the electrodes are in situ, by activating an arming circuit, which allows pulsing to begin when the START button is pressed.

Pulsing activity is indicated by the flashing of PULSING LED 64 and the synchronous activation of audible alarm 66.

The ENABLED state or PULSING state can be interrupted at any time by pressing RESET button 60. This action deactivates the pulsing, extinguishes LEDs 64, 62, 54 and audible alarm 66 and resets controller 46 to an initial state. If the PULSING state is not interrupted, controller 46 directs constant-current source 42, and current switch 32 to deliver current pulses to electrodes 22 of an intensity, duration and count, as determined by the settings of input devices 36, 38 and 34.

The building-blocks in FIG. 5 can be implemented by state-of-the-art technology, known to any person skilled in the art of electronics. For example Controller 46 can comprise a microprocessor, a microcontroller or discrete integrated circuits. Similarly, the selector switch 26 and current switch 37 may comprise electromechanical switches or semiconductor switches. Constant-current source 42 may comprise discrete components or an off-the-shelf Application Specific Integrated Circuit ("ASIC"). A marked drop with tissue impendence occurs following electroporation pulse, which requires the current to be increased.

A number of variables are considered in achieving a desired current pulse for the circuit. For example, the Power supplies 24 and 42 may use linear or switching technology. Battery 52 may use gel-cell or lithium ion technology input devices 34, 36 and 38 may comprise potentiometers or digital switches, readable by controller 46. The invention requires power supplies that can deliver a range of from about 0.005 kV to about 1 kV, depending on the need. Electrode assembly 22 may comprise a plurality of needle electrodes adapted to be inserted into tissues, metallic, or non-metallic, electrodes designed to make galvanic contact with the skin, or electrodes adapted to be inserted into containers holding material to be treated.

Figure 6:
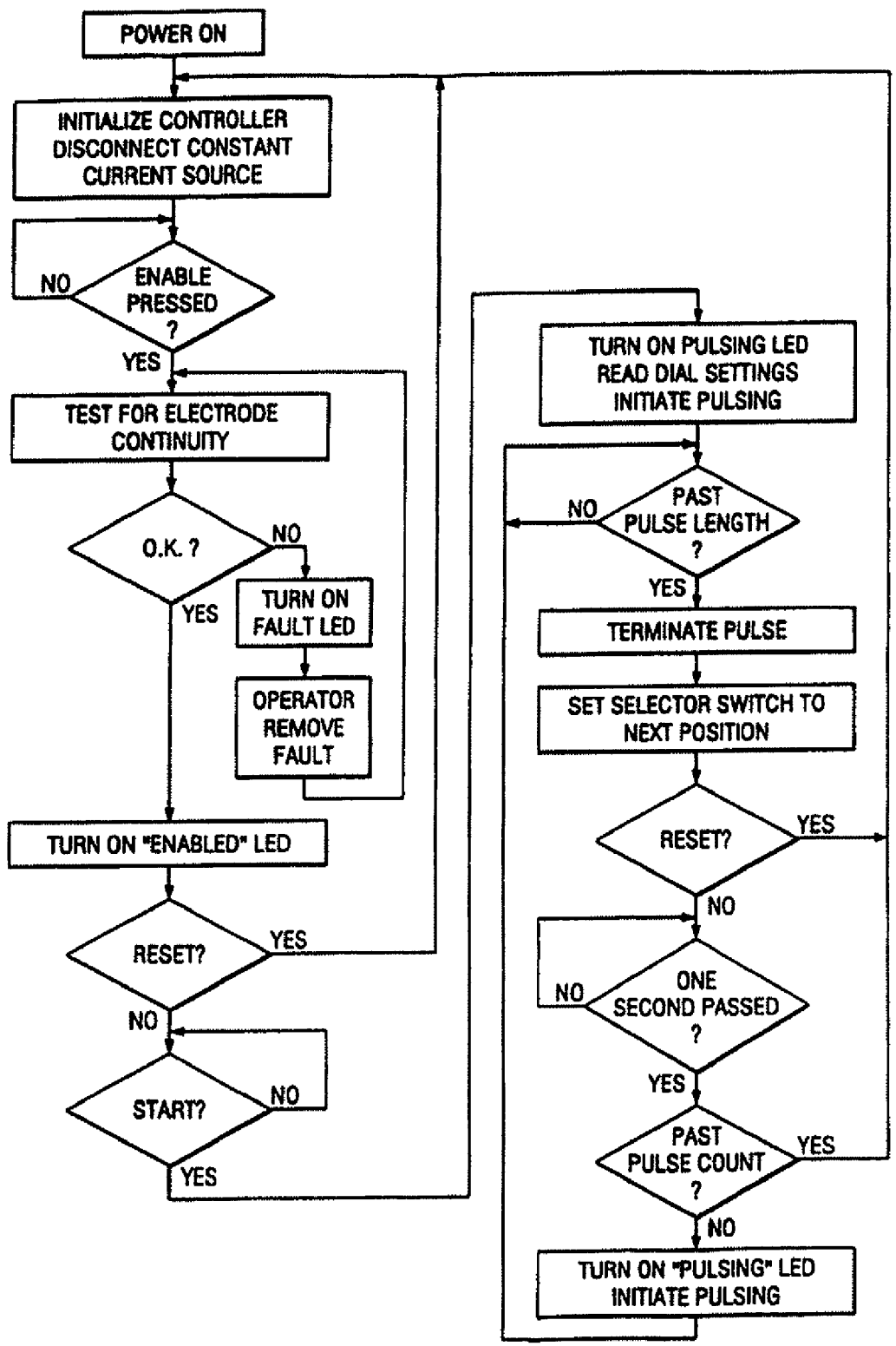
FIG. 6 shows a flow chart of the logic steps responsible for behavior of the programmable constant-current pulse controller.

FIG. 6 shows the sequence that operator input is processed by the controller. Other sequences and predetermined parameters, such as the time interval between the pulses, could be implemented within the scope of the present invention.

EXAMPLE 1

Prototype Specifications and Operating Instructions

One embodiment of the present invention is the model XEP-100 electroporator prototype. It has an input power of 117 volts and an output voltage that is selectable from 100 to 200 volts with a front panel switch, and a voltage accuracy of plus or minus ("±") 2%. The output current for this device is 8 amperes into a 25 ohm load. The output current fuse is a 15 amperes slow blow. The pulsing frequency is 1 Hz, with the pulse length set a 50 mS. A maximum leakage current of 8 µA should prevent potential fatal accidental exposure. The pulse configuration is six sequential pulses of alternating polarity. The prototype has dimensions of 15×30.5×34 cm, with a weight of 6.2 kg. The entire device is encased in a shock resistant watertight case.

The XEP-100 prototype for a modular electroporation system used for facilitating the introduction of a macromolecule into cells of a selected tissue in a body or plant has been constructed and a protocol for the working operation of the prototype is described below. Initially a needle electrode assembly is connected to a constant-current pulse generator subsystem FIG. 7. The needle electrode assembly (as shown in FIG. 3) is adapted to deliver the macromolecules through a hypodermic needle, and deliver a constant-current electrical pulse through a plurality of needle electrodes to the selected tissue. An electrical connector (FIG. 4) that provides a conductive link form the pulse controller (FIG. 7) to the needle electrodes is constructed as a handle and is designed to easily mount the needle electrode assembly. One embodiment of the invention envisions a human operator grasping the handle and firmly insert the mounted needle electrode assembly into the selected tissue of the subject. The macromolecules are then delivered via the hypodermic needle into the selected tissue of a subject and activation of the programmable current pulse controller will distribute a constant-current electrical pulse to the plurality of needle electrodes. The constant-current electrical pulse is a decentralized electroporation event that occurs in an area where no congruent electroporation overlap points develop, which allows the macromolecule to be inserted into the cell of the subject without overheating and damaging the cell or tissue, as described above in FIGS. 1 and 2.

Figure 7:
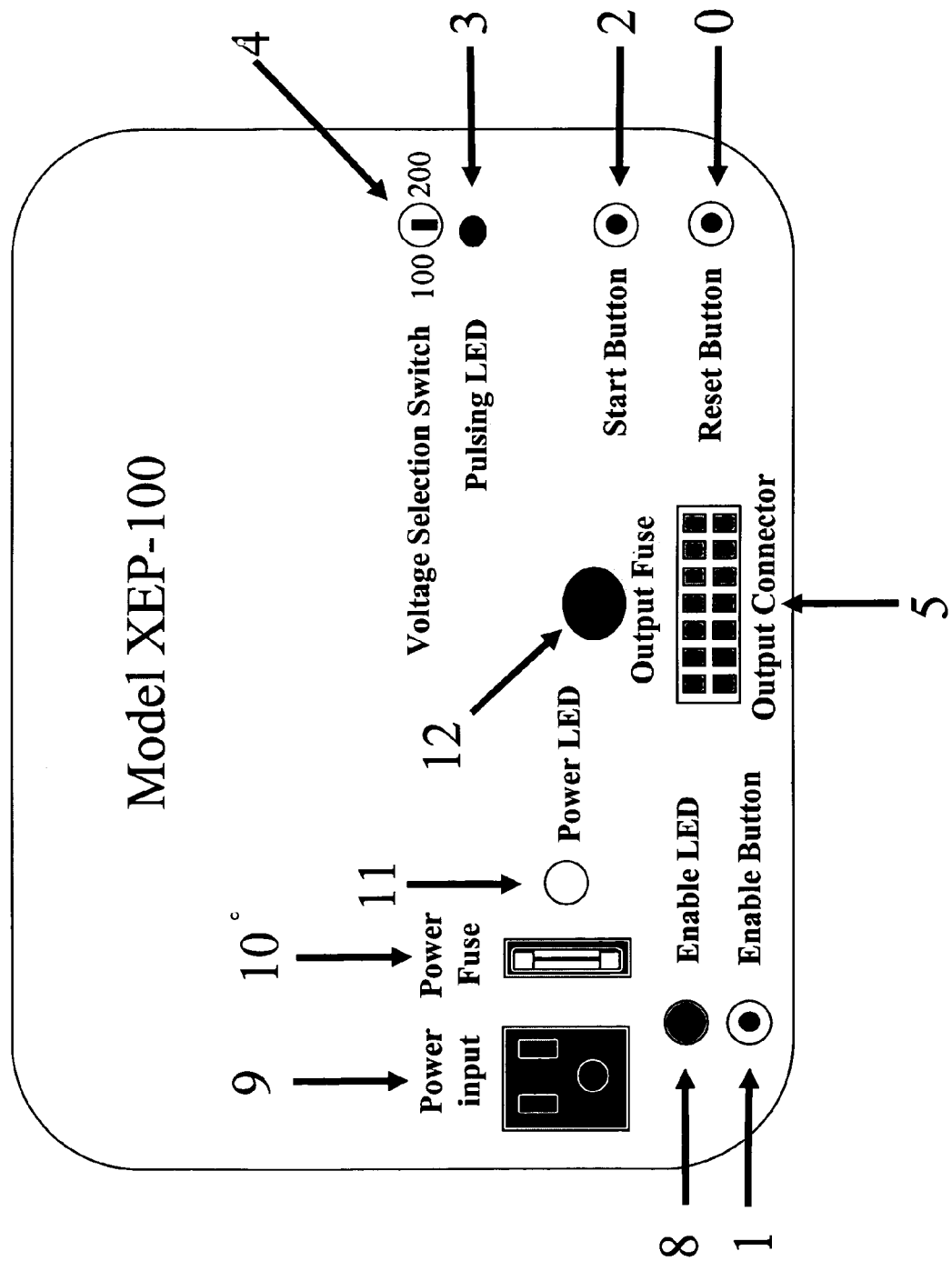
FIG. 7 show the front panel of an XEP-100 programmable constant-current pulse generator subsystem prototype.

As shown in FIG. 7, the initiation of the electroporation event begins with inserting the needle electrode assembly and the desired macromolecules into a muscle tissue of a subject. The VOLTAGE SELECTION SWITCH (1) on the XEP-100 prototype is set to the desired voltage, either 100 or 200V. Next the power switch for the XEP100 prototype is turned on, and the lit white LED (11) will confirm power. The operator will need to wait 5 seconds to allow the electronic circuits to stabilize. During this interval, the ENABLE button (1) is inoperative. When the operator is ready to use the instrument:

1) Press the ENABLE button (1). The orange LED (8) will be lit to indicate that pulsing can start.

2) Press the START button (2) to initiate pulsing. A flashing blue LED marks each pulse. After 6 pulses, both the orange "ENABLED" LED and the blue "PULSING" LED are extinguished.

The procedure can be interrupted at any time by pressing the red RESET button (0). After a resetting, 5 seconds must pass before normal operation can be resumed. Because the pulses occur at one-second intervals, the START button may have to be held down as long as one second to allow pulsing to be synchronized with the internal clock. When the electroporator is pulsed without a load, or when an electrode pin is broken, abnormally high voltage spikes may cause the pulse counter to miscount. This can be remedied by pressing the RESET button (0) before normal operation is resumed. This incurs a 5 second waiting period before the unit can be enabled again.

An electroporator is an inherently dangerous device, and extreme caution must be exercised when using it. There are particular hazards that should be given specific attention. For example high voltages are present at the needle electrodes that can cause severe burns if accidental skin contact occurs. However, if skin contact does occur, the involuntary muscle movement caused by the shock may result in further injury. Electric sparks may be generated during normal operation of the device, which could ignite an explosive atmosphere. When the operator completes a conductive path between the electrodes and ground, a "leakage current" at the power line frequency flows through the body. The magnitude of this current is limited by design to 2 microamperes when the unit is energized from a properly grounded power outlet. However, when the unit is connected to an outlet with a faulty grounding pin, the current may reach 8 microamperes. Although these values are well below the 80 microampere threshold that may induce ventricular fibrillation, care should be taken not to touch a grounded operating table when using the instrument. When standing on a conductive floor or moist soil, the operator should wear shoes or boots with rubber soles. Additionally if two electrodes touch, or the electrode assembly contacts a metallic object when pulsing the excessive current can melt the electrodes and spattering molten metal, which can cause severe burns. Therefore, care should be taken to avoid touching the electrodes to metallic objects.

EXAMPLE 2

Predetermined Voltage vs. Constant-Current

Figure 8:
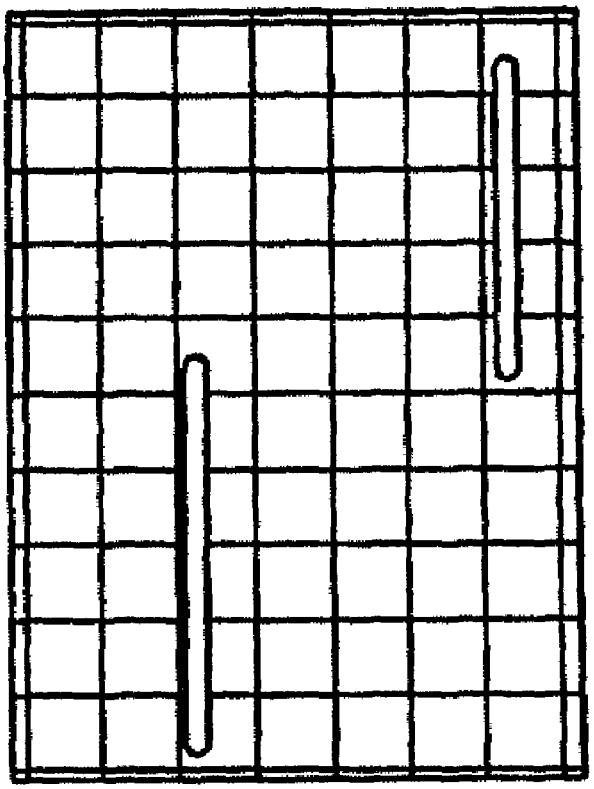
FIG. 8 shows how a predetermined voltage pulse causes an increase in the current flowing through a porcine muscle tissue during the duration of the pulse, in contrast a constant-current source actually maintains a constant-current through a porcine muscle tissue.
Figure 8:
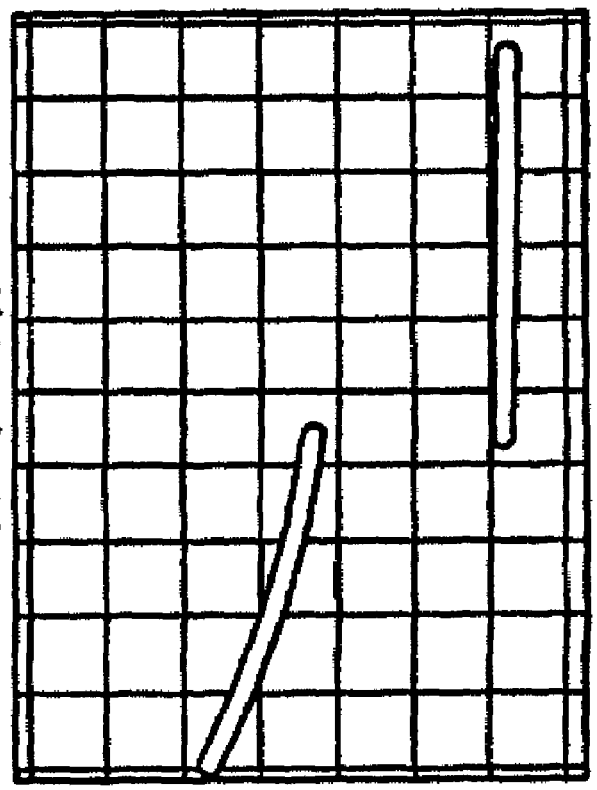

In order to demonstrate the advantages between prior art and the current invention, an electroporation experiment was conducted in a porcine muscle. In a prior art system where a predetermined voltage has been imposed on the electrodes, the current increases at the moment of electroporation. Although not wanting to be bound by theory, the current increase is due to an increased cell permeability that lowers the interelectrode impedance. In one trail needle electrodes were imbedded in the porcine muscle and a 50 mS pulse was delivered to the muscle tissue, which resulted in an approximate 5 Amperes increase in current in the porcine muscle tissue (FIG. 8A). This may lead to an excessive temperature rise and results in cell death. The rise in temperature can be calculated by utilizing values common for conventional prior art electroporators, and assuming that the volume enclosed by the electrodes is one cubic centimeter and the specific heat of the tissues is close to unity, the temperature rise owing to one 50 mS pulse with an average current of 5 Amperes across a typical load impedance of 25 ohms is approximately 7.5° C. This points out the necessity of inserting an adequate delay between successive pulses, to allow the subjects circulatory system to remove enough heat so that the cumulative temperature rise will not result in destruction of the tissues being electroporated.

In contrast, the advantage of a constant-current system is that the current can be prevented from attaining an amplitude at which the cells are destroyed. For example a 50 mS pulse in a constant-current system results in no net increase in Amperes in the porcine muscle (FIG. 8B). Accordingly there is no net increase in heat, which assures cellular survival. Pulsing cannot alter the current because the current is preset at a level where cell death does not occur.

The above examples show the difference in current flow through a porcine muscle tissue for a pulse of predetermined voltage and a pulse of constant-current. FIG. 8A demonstrates that the current changes in muscle tissue as a pulse of predetermined voltage is passed through a porcine muscle tissue. In contrast, FIG. 8B demonstrates that a constant-current is actually maintained in the during a pulse of a constant-current pulse generated by the constant-current system of the present invention. Thus, the present invention maintains a constant-current through tissues and prior art does not. Additionally, similar experiments were completed on bovine muscle tissue and a saline solution sample. In each experiment, all the results showed the same characteristics. Therefore, the current is not altered as it passes from plus to minus in a selected tissue. The current traverses any and all obstacles provided that the pressure of voltage behind the current is large enough. However, should the electrode impedance rise to a very high value, as typically happens when the tissue surrounding the electrodes are charred, then the constant-current source will "run out of voltage", and the current will decrease. This will protect the tissues from any further damage, and protect the electroporator from electrical damage. Consequently, the electrodes of the present invention can be short-circuited (e.g. as occurs when two or more electrodes are contacted simultaneously with a metallic operating table) and no damage will result.

Although syringe injection followed by in vivo constant-current electroporation is the preferred method for delivering the macromolecules into the cells of the subject, other suitable methods for macromolecule delivery to an organelle, a cell, a tissue or an organism can be complemented with combinatorial use with the current invention. Virtually any method by which a macromolecule can be introduced into an organelle, a cell, a tissue or an organism, as described herein or as would be known to one of ordinary skill in the art could be used in combination with the present invention. Such in vivo as well as ex vivo methods include, but are not limited to, microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (U.S. Pat. Nos. 4,684,611 and 4,952,500, each incorporated herein by reference); by desiccation/inhibition-mediated DNA uptake, and any combination of such methods used in conjunction with constant-current electroporation.

Another embodiment of the invention is to perform an electrofusion of drug-loaded vesicles to a specific tissue in a subject. Drug loaded vesicles are introduced into a specific tissue in the center of a plurality of needle electrodes, a constant-current pulse is then used to create a dielectric breakdown of a specific tissue surface forming passage through which the drugs and genes are transferred from the vesicles through into the tissue. The constant-current pulse would be generated by utilizing a programmable current pulse controller that will transfer the constant-current pulse between any two electrodes of the plurality of needle electrodes. This method will minimize an impedance between the electrodes and prevent cell death due to heating. This method would also take advantage of the electro fusion of microbubbles to transfer drugs and genes across the surface tissue and possibly into the blood stream and, if desirable, subsequent electroporation into underlying tissue.

It should also be understood that numerous changes and modifications of the electrode assembly itself may be made therein without departing from the spirit and the scope of the invention as defined in the claims. For example, another embodiment, the invention provides a method for delivery of a macromolecule to a cells that make up the blood vessel walls or simply cells in culture. With modifications, the needle electrode array could be converted into a catheter electrode array that is connected to the same programmable current pulse controller and power supplies described herein. The catheter could be placed inside a blood vessel and macromolecules could then be delivered directly into the vessel wall utilizing a constant-current protocols described herein, which would not overheat or destroy the wall of the blood vessel. The constant-current pulse would be generated by utilizing a programmable current pulse controller that will transfer the constant-current pulse between any two electrodes of the plurality of needle electrodes. This method will cause cell death due to heating. Such an apparatus and method would be an excellent mechanism for direct and more regulated delivery of macromolecules into the blood stream.

The constant-current pulse generated by a programmable current pulse controller transfers the constant-current pulse between any two electrodes of the plurality of needle electrodes without heating the tissues. It is further understood that the use of any form of electromagnetic radiation that is capable of electroporation of cells can also generate heat. One skilled in the art will appreciate the ability to slightly modify the programmable current pulse controller to other forms of electromagnetic radiation used for electroporation such that the high amplitude heating is minimized when using a controller circuit as described in herein and in FIG. 4. For example, to induce cell-poration or cell-fusion, a high power function generator can produce one or more high power radio-frequency pulses that can be applied through the pair of electrodes. The radio-frequency pulse can be used because it allows the applied energy of the field to contain more than one Fourier component and is efficient in inducing cell poration or fusion, as indicated in U.S. Pat. No. 4,822,470, which is herby incorporated by reference. However, heating of the tissues may result, therefore adaptation of the current pulse controller system of the present inventions would allow one to monitor the impedance of tissue between the electrodes and adjust the radio frequency accordingly to prevent heating of tissue between electrodes.

Figure 9:
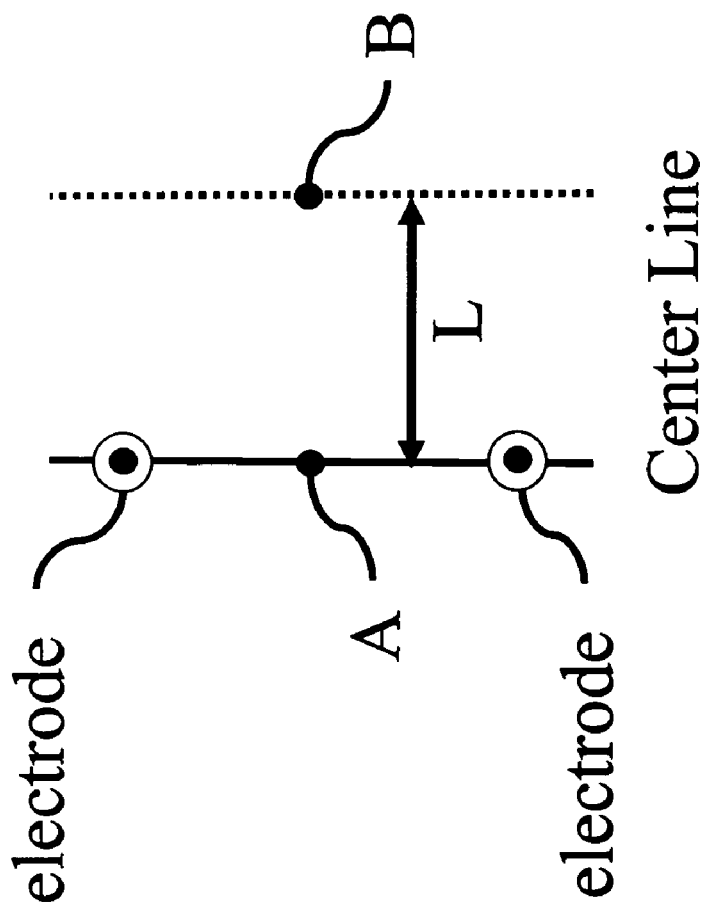
FIG. 9 shows the voltage imposed on electrodes in a conductive medium.

An electrode assembly with a more uniform energy distribution is devised can be achieved as follows:

When voltage is imposed on electrodes in a conductive medium, as shown in FIG. 9, the maximal current intensities are found at point that lie on the line joining the electrodes. Points at a distance L from the line experience current intensities that are inversely proportional to L. Thus, at some distance L the current at point B is one half of the intensity at point A.

Figure 10:
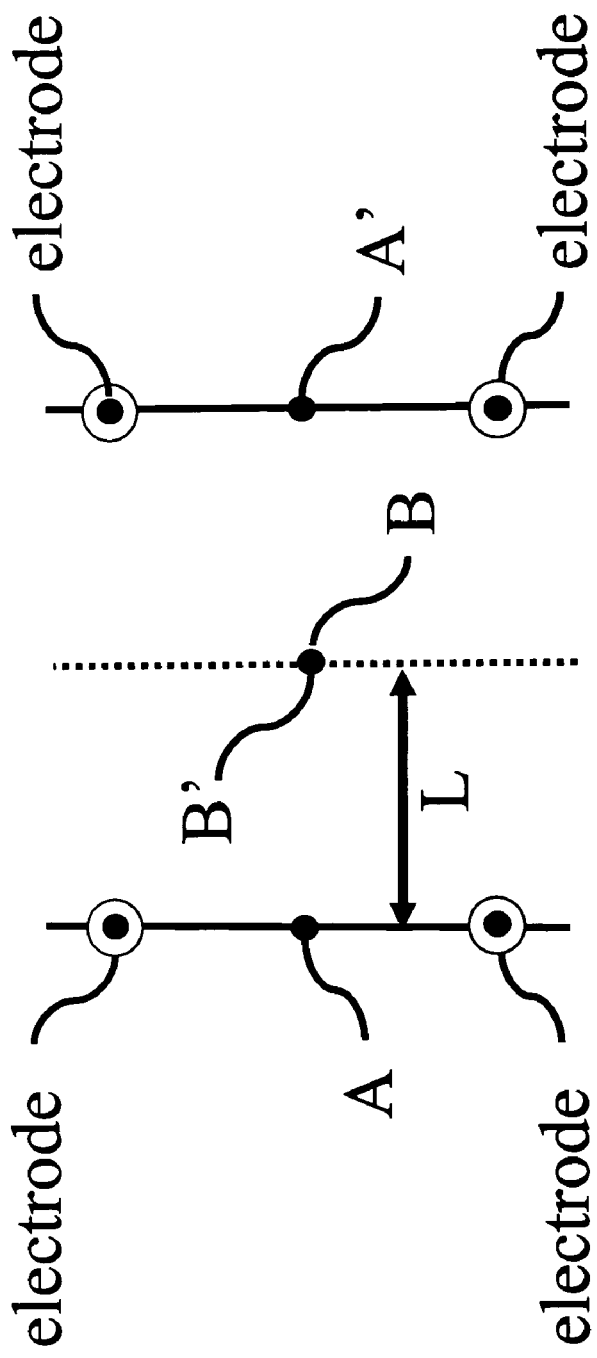
FIG. 10 shows two electrode pairs, side-by-side, separated by distance 2L.

The addition of more electrodes to the scenario outlined in FIG. 9 results in a different energy distribution profile. For example, when two pairs of electrodes are placed side by side and separated by a distance 2×L, the resultant energy at point B equals that of point A, as shown in FIG. 10. This is similar to the one used to obtain an electrical filter with a flat response, by stagger-tuning individual circuits with peak response curves.

Figure 11:
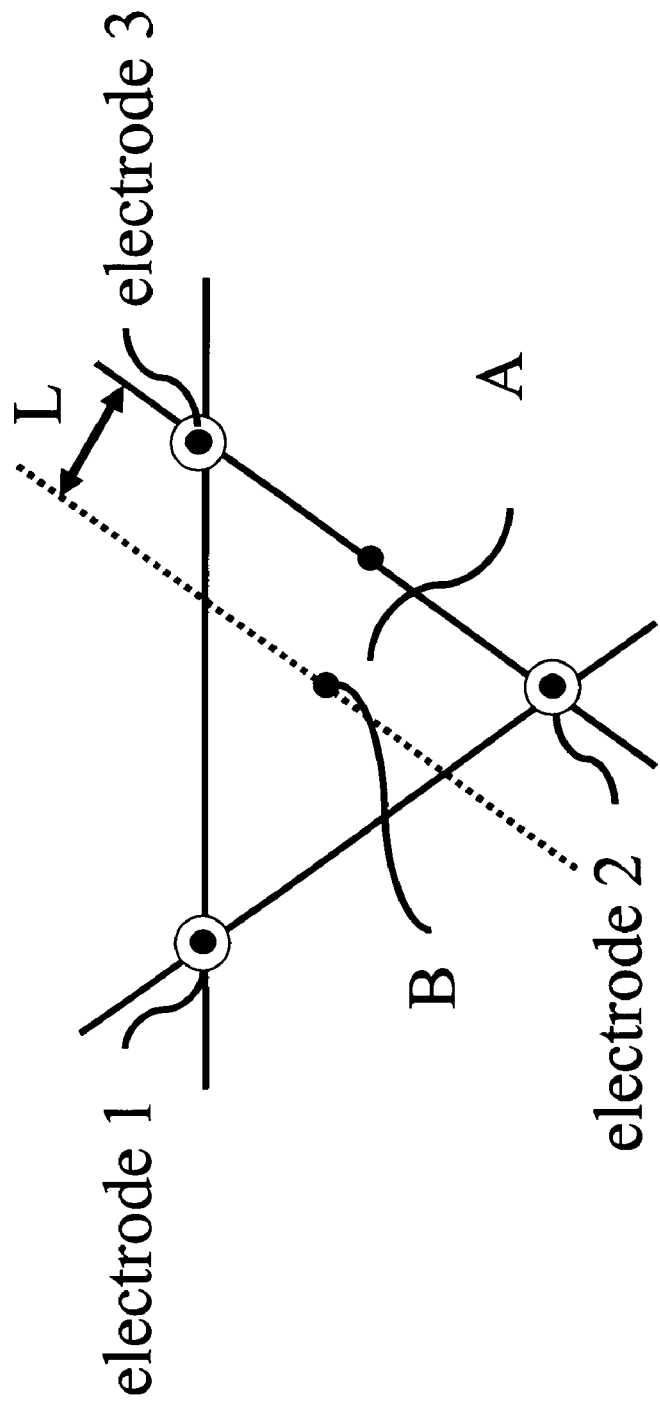
FIG. 11 shows a three-electode array, where distance L=k× n, and n is the number of electrode and k is a proportionality constant.

The concept can be extended to any number of electrodes. FIG. 11 shows a three-electrode array. The distance L is chosen so that the energy intensity at point B is one third of that at point A. After three pulses, (1 to 2, 2 to 3 and 3 to 1), point B has received a cumulative dose equal to that of point A.

As the number of electrodes in the array are increased, the distance L necessary to yield a uniform energy distribution becomes proportionately longer. $L=k \times n$ where n is the number of electrodes, and k is a proportionality constant. Thus, by selecting a greater number of electrodes a greater volume of tissue can be encompassed.

The optimal number of electrodes chosen may depend on the volume of the material to be transfected and how far it is dispersed between injection and electroporation.

One aspect of the present invention is a modular electrode system for introducing macromolecules into one or more cells of an animal or plant. The components of the system include a plurality of needle electrodes mounted on a support structure with a configuration for penetrating the selected tissue. In a preferred embodiment, the macromolecule are injected into the selected tissue with a syringe. Together the plurality of needle electrodes and support structure form a needle electrode assembly that can be mounted on a handle. The handle also contains an electrical connector from the needle electrode assembly to a constant-current pulse generator subsystem. The handle is designed to provide a user an easy means for implanting the needle electrode assembly into a selected tissue. The utilization of disposable needle assembly and snap-on mounts on the handle allows a user to quickly attach and detach the needle electrode assembly.

Another embodiment of the present invention is a method for introducing macromolecules into one or more cells of a selected tissue in a living body or plant, which utilizes the modular electrode system described herein. In a preferred embodiment of this invention, the modular electrode system and method allows an operator to grasp the handle of the constant-current pulse generator subsystem, attach the needle electrode assembly, and firmly insert the needle electrodes into the selected tissue. The macromolecules are then delivered into the selected tissue of an animal or plant. A syringe with a specially designed macromolecule injection cartridge can be used delivering a single dose concentration of presterilized macromolecules in a body or plant comprising. In a preferred embodiment this macromolecule injection cartridge comprises a plastic container portion that contains the single dose concentration of presterilized macromolecules, and a presterilized hollow sharp needle extending from the plastic container portion that will convey fluids from within the container out through the tip of the hollow needle when the needle is inserted into the body or plant. The activation of the programmable current pulse controller will distribute a constant-current electrical pulse to the plurality of needle electrodes such that a decentralized electroporation event occurs in an area where no congruent electroporation overlap points develop. The permeability of the cells in the area of decentralized electroporation increases and the macromolecule are delivered into the cell of the subject without overheating and damaging the cell or tissue. A further embodiment of the present invention is the portability of the constant-current pulse generator subsystem that allows one to utilize battery packs for use in the field where access and use of a plug in power source is dangerous or inconvenient.

EXAMPLE 3

Electroporation on Pigs

Different muscles have different tissue resistance due to differential muscle fiber density, fat protein and collagen content, fascia distribution, and thickness. The level of injected plasmid expression is dependent on the tissue resistance. If the injected muscle suffer considerable damage, the level of plasmid expression drops. In the following example, all animals were injected using the 6 needle array electroporation system/200V/cm, 6 pulses, variable orientation.

Figure 12:
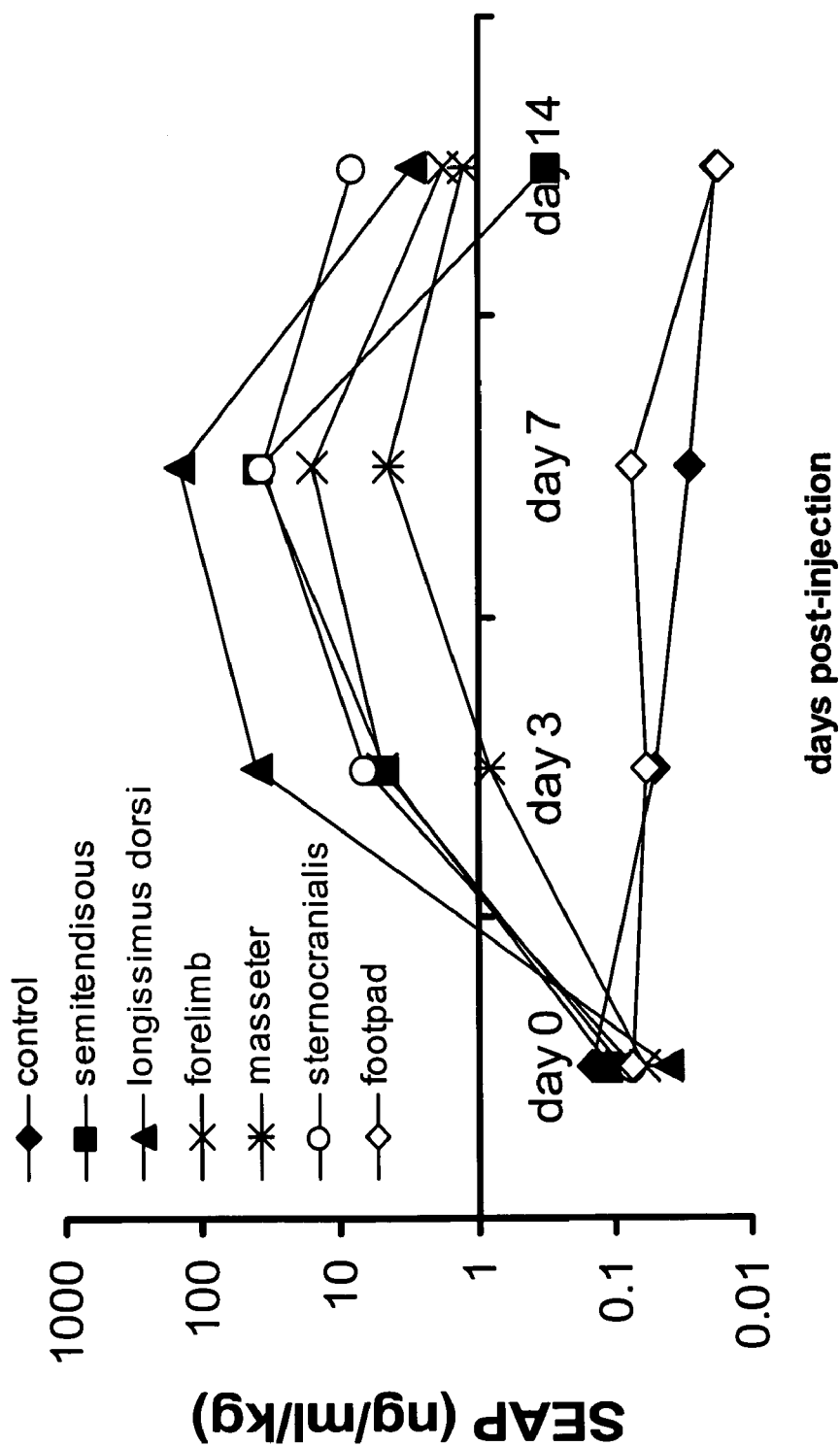
FIG. 12 shows SEAP values in pigs injected with 5000 mcg SP-SEAP construct into different skeletal muscles.

Secreted embryonic alkaline phosphatase ("SEAP") values in pigs injected with 500 mcg synthetic promoter-SEAP ("SP-SEAP") construct into different skeletal muscles are shown in FIG. 12.

EXAMPLE 4

Electroporation on Pigs Using 5- and 6-Needle Array Electrode

Figure 13:
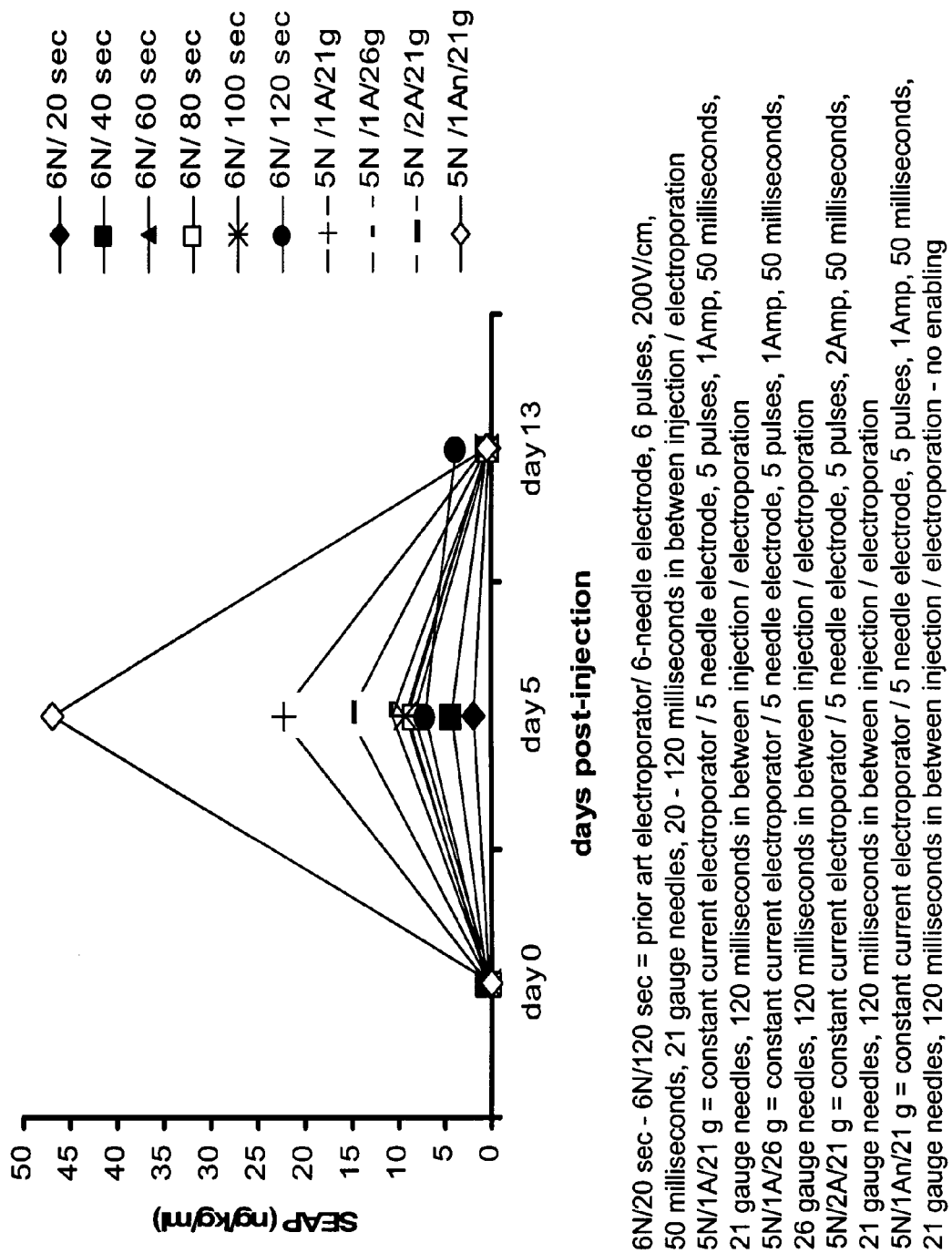
FIG. 13 shows SEAP values in pigs injected with 55 mcg SP-SEAP into the sternocranialis muscle of young pigs.

Five hundred micrograms SP-SEAP was injected into the sternocranialis muscle of young pigs. The injection was followed by electroporation using either the 6-needle ("6N") voltage-based electroporation system (at different time points after the injection) or the constant-current electroporation system of the present invention, using the 5-needle ("5N") electrodes (FIG. 13). The condition used for each individual group are listed.

Serum samples were collected before the injection and at 5 and 13 days post injection. Weights were recorded at the same time points. SEAP is immunogenic in pigs, and the expression disappears after day 7-10 post-injection. The results show that the constant-current electroporation system gives 3-8 the expression level of the voltage-based electroporation system.

What is claimed:

1. A modular electrode system for introducing of a macromolecule into a muscle tissue in a body, comprising: a plurality of needle electrodes for penetrating the muscle tissue, the plurality of needle electrodes being mounted on a support structure and arranged non-symmetrically around a center point, and a constant-current pulse generator subsystem in electrical communication with the plurality of needle electrodes, wherein the constant-current pulse generator subsystem is capable of applying a decentralized constant-current pulse between any plurality of electrodes and the plurality of needle electrodes are constructed from a material that will make galvanic contact with the tissues; and a programmable constant-current pulse controller having an impedance meter in electrical communication with the plurality of needle electrodes and the constant-current pulse generator subsystem, wherein the programmable constant-current pulse controller is capable of maintaining a constant current independent of any resistance change in the muscle tissue during the decentralized constant-current pulse.

2. The modular electrode system of claim 1, further comprising macromolecule injection cartridge for delivering a single dose concentration of pre-sterilized macromolecules into a muscle tissue in a body comprising: a plastic container portion that contains the single dose concentration of pre-sterilized macromolecules, and a pre-sterilized hollow sharp needle extending from the plastic container portion that will convey fluids from within the container out through the tip of the hollow needle when the needle is inserted into the body or plant, wherein the pre-sterilized hollow sharp needle is capable of being placed around the center point of plurality of needle electrodes for the purpose of injecting macromolecules.

3. The modular electrode system or claim 1, wherein the macromolecules are nucleic acids, plasmids, polynucleotides, proteins, peptides, proteinaceous compositions, amino acid chains, lipids, mimetics, or pharmaceuticals in a fluid medium.

4. The modular electrode system of claim 1, wherein the constant-current pulse generator subsystem comprises: (a) an electrical connector that provides a conductive link from a pulse controller to the plurality of needle electrodes; and (b) the programmable current pulse controller in electrical communication with a power source.

5. The modular electrode system of claim 4, wherein the electrical connector comprises a handle designed with a mount structure for fastening the plurality of needle electrodes to the handle and the handle contains a protective electrical insulating material to protect an operator from an electrical shock.

6. The modular electrode system of claim 5, wherein the mount structure positions the plurality of needle electrodes in a position that allows the handle to be used as a pushing tool to aid in the penetration of the plurality of needle electrodes into the muscle tissue, wherein the handle allows a hypodermic needle to be used for introducing the macromolecule into the muscle tissue in an area inside the plurality of needle electrodes.

7. The modular electrode system of claim 5, wherein the plurality of needle electrodes fastened to the mount are released by a quick-release mechanism.

8. The modular electrode system of claim 5, wherein the handle contains a switch that allows the user to initiate the constant-current pulse to the needle electrode assembly.

9. The modular electrode system of claim 4, wherein the power source is portable.

10. The modular electrode system of claim 4, wherein the power source provides both high-voltage and low-voltage power to the programmable current pulse controller.

11. The modular electrode system of claim 4, wherein the programmable current pulse controller comprises: a switching mechanism for transferring a constant-current pulse between any two electrodes of the plurality of needle electrodes and a current pulse controller circuit; the current pulse controller circuit for applying a pulse of constant-current from the power source to the switching mechanism and maintaining a constant-current throughout the duration of a timed pulse; and an input device for programming a logical sequence of coded instructions to the current pulse controller circuit.

12. The modular electrode system of claim 11, wherein the input device comprises: a current level input; a pulse length input; and a pulse count input.

13. The modular electrode system of claim 11, further comprising an impedance meter for relaying impedance information between any two electrodes of the plurality of needle electrodes and the current pulse controller circuit.

14. The modular electrode system of claim 11, wherein the programmable current pulse controller generates a constant-current pulse in a path between any two electrodes.

15. The modular electrode system of claim 11, wherein the programmable current pulse controller generates one or more high power radio frequency pulses that are applied in a path between any two electrodes.

* * * * *